US010088420B2

(12) United States Patent
Okabe et al.

(10) Patent No.: US 10,088,420 B2
(45) Date of Patent: Oct. 2, 2018

(54) MEASUREMENT SYSTEM AND METHOD FOR SWITCHING SET VALUE FOR ADJUSTMENT (71) Applicant: Mitutoyo Corporation, Kawasaki, Kanagawa (JP)

(72) Inventors: Kenji Okabe, Kanagawa (JP); Tatsuya Nagahama, Kanagawa (JP); Nobuya Kaneko, Kanagawa (JP)

(73) Assignee: MITUTOYO CORPORATION, Kawasaki (JP)

( * ) Notice: Subject to any disclaimer, the term of this patent is extended or adjusted under 35 U.S.C. 154(b) by 0 days.

(21) Appl. No.: 15/597,856

(22) Filed: May 17, 2017

(65) Prior Publication Data
US 2017/0336327 A1    Nov. 23, 2017

(30) Foreign Application Priority Data
May 23, 2016    (JP) .................................. 2016-102082

(51) Int. Cl.
*G01N 21/64*    (2006.01)
(52) U.S. Cl.
CPC ...... *G01N 21/6456* (2013.01); *G01N 21/6489* (2013.01); *G01N 2021/6471* (2013.01); *G01N 2201/024* (2013.01)
(58) Field of Classification Search
CPC ......... G02B 26/007; G01N 2021/6471; G01N 21/6456; G01N 21/6489
USPC ..................................................... 250/458.1
See application file for complete search history.

(56) References Cited

U.S. PATENT DOCUMENTS

| | | | | |
|---|---|---|---|---|
| 6,606,115 B1* | 8/2003 | Alicandro | ............. | G01J 5/0066 250/230 |
| 2006/0092503 A1* | 5/2006 | Saunders | ........... | G02B 21/0008 359/368 |
| 2010/0091089 A1* | 4/2010 | Cromwell | ............. | G03B 11/00 348/33 |
| 2011/0069199 A1* | 3/2011 | Yamazaki | ............. | A61B 1/0005 348/229.1 |
| 2011/0102566 A1* | 5/2011 | Zakian | ................. | A61B 5/0075 348/66 |
| 2012/0153152 A1* | 6/2012 | Okabe | .................. | G02B 21/248 250/338.1 |
| 2012/0264226 A1* | 10/2012 | Unger | .................... | G02B 21/36 436/172 |
| 2013/0050705 A1* | 2/2013 | Yli-Koski | .......... | G01N 21/6445 356/432 |
| 2013/0175457 A1* | 7/2013 | Wada | ................... | G01N 21/648 250/459.1 |

(Continued)

FOREIGN PATENT DOCUMENTS

JP    2012-128295    7/2012

*Primary Examiner* — Taeho Jo
(74) *Attorney, Agent, or Firm* — Rankin, Hill & Clark LLP (57) ABSTRACT A measurement system includes detachable parts, on which one filter module out of a plurality of filter modules including optical filters that each transmit different types of special light is detachably mounted, a specification part that specifies the optical filter of the one filter module mounted on the detachable parts, and a set value switching part that switches, according to the specified optical filter specified by the specification part, set values for adjustment used in a measurement using a specific optical filter.

15 Claims, 9 Drawing Sheets (56) References Cited

U.S. PATENT DOCUMENTS

| | | | |
|---|---|---|---|
| 2013/0242383 A1* | 9/2013 | Kusaka | G02B 21/0076 359/370 |
| 2013/0286190 A1* | 10/2013 | Xin | H04N 5/33 348/126 |
| 2014/0027653 A1* | 1/2014 | Mori | G02B 5/22 250/458.1 |
| 2014/0078285 A1* | 3/2014 | Mitsui | H04N 9/045 348/79 |
| 2014/0145084 A1* | 5/2014 | Okabe | G02B 21/248 250/353 |
| 2015/0042983 A1* | 2/2015 | Cohen-Erner | G01N 21/9501 356/73 |
| 2015/0153564 A1* | 6/2015 | Sano | G02B 26/001 359/578 |
| 2015/0212313 A1* | 7/2015 | Hirokubo | G02B 26/001 359/578 |
| 2015/0212314 A1* | 7/2015 | Kuri | G02B 26/001 359/578 |
| 2015/0244949 A1* | 8/2015 | Laroia | H04N 5/2352 348/296 |
| 2016/0156822 A1* | 6/2016 | Iwasaki | G02B 23/2461 348/68 |

* cited by examiner

MEASUREMENT SYSTEM AND METHOD FOR SWITCHING SET VALUE FOR ADJUSTMENT

CROSS-REFERENCE TO RELATED APPLICATIONS

The present application claims priority to Japanese Patent Application number 2016-102082, filed on May 23, 2016. The content of this application is incorporated herein by reference in its entirety.

BACKGROUND OF THE INVENTION

The present invention relates to a measurement system and a method for switching set values for adjustment.

In recent years, as an optical measurement system, a measurement system that is capable of performing a special measurement, in which special light such as infrared light is radiated onto a workpiece to be measured, is used in addition to visible measurement, in which visible light is radiated onto a workpiece to be measured. For example, Japanese Unexamined Patent Application Publication No. 2012-128295 discloses an optical measurement device having both a visible observation part for performing a visible observation (the visible measurement) of a workpiece and a special observation part for performing a special observation (the special measurement) of a workpiece.

In order to realize a special measurement, it is necessary to control the wavelength of light and the like, and such control is performed, for example, by an optical filter. For this reason, in order to realize a plurality of special observations with a single measurement apparatus it is necessary to mount optical filters corresponding to each of a plurality of special lights in the apparatus, and so the number of special observations that can actually be performed is limited. Further, when a special measurement is switched to another special measurement, it is necessary to adjust complicated set values according to the optical filter, and so the switching takes a long time.

BRIEF SUMMARY OF THE INVENTION

This invention focuses on these points, and an object of the invention is to realize a plurality of special measurements with a single device and to make it easier to adjust set values according to optical filters.

In one aspect of the present invention, a measurement system that comprises detachable parts, on which one optical filter module out of a plurality of optical filter modules including optical filters that each transmit different types of special light is detachably mounted, a specification part that specifies the optical filter of the one optical filter module mounted on the detachable parts, and a set value switching part that switches a set value for adjustment used in a measurement using the optical filter in accordance with the optical filter specified by the specification part is provided.

DETAILED DESCRIPTION OF THE INVENTION

<Outline of a Measurement System 1>

Figure 1:
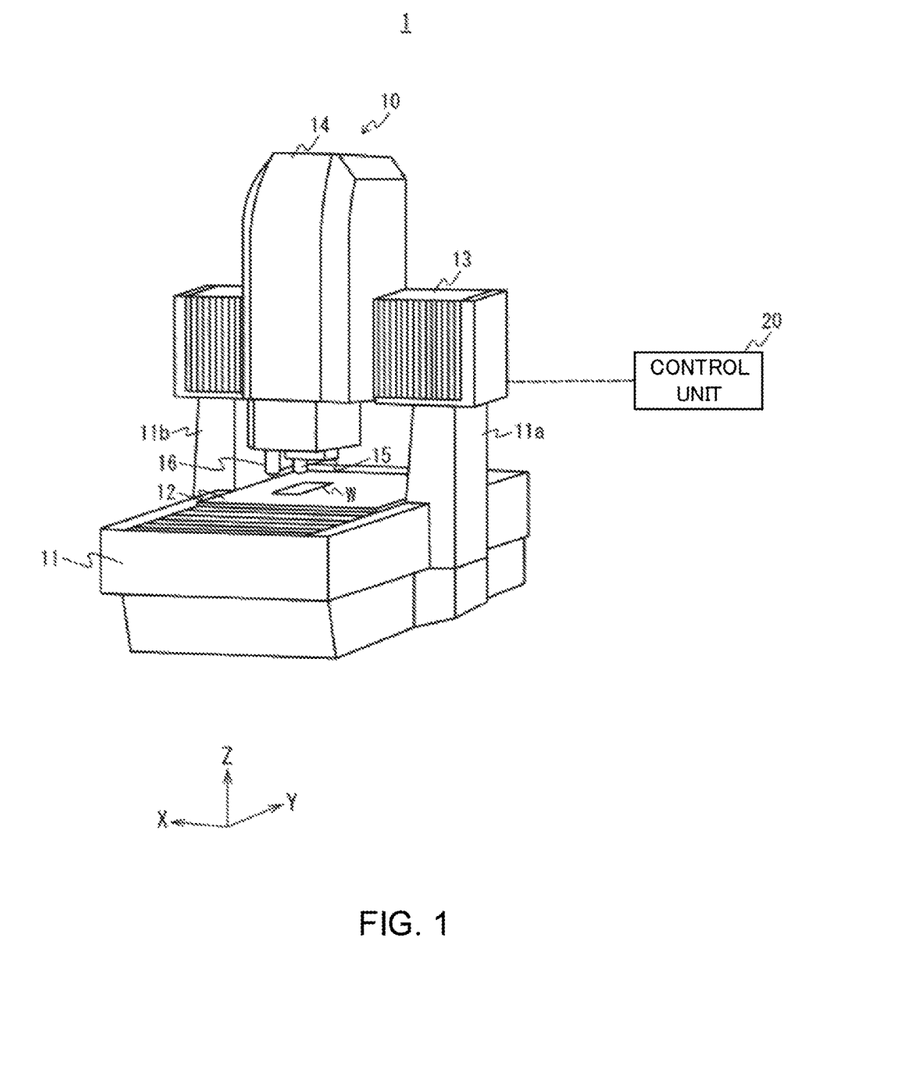
FIG. 1 is a diagram showing an example of a configuration of a measurement system 1 according to one exemplary embodiment of the present invention.

A configuration of a measurement system 1 according to one exemplary embodiment of the present invention is described with reference to FIG. 1. FIG. 1 is a diagram showing an example of the configuration of the measurement system 1 according to one exemplary embodiment.

The measurement system 1 acquires an image of an object to be measured by irradiating the object with a light, and measures the size, height, shape, and the like of the object. The system 1 is able to acquire an image both by visible light and by special light so that the system 1 can measure various kinds of objects. As shown in FIG. 1, the measurement system 1 includes a vision measuring machine 10 and a control unit 20.

The vision measuring machine 10 includes a stand 11, a stage 12, an X-axis guide 13, a moving unit 14, a first measurement part 15, and a second measurement part 16.

The stand 11 is a base portion of the vision measuring machine 10. The stand 11 is arranged, for example, on a vibration resistant table for suppressing transmission of external vibrations.

The stage 12 is arranged on the stand 11. A workpiece W, which is an object to be measured, is placed on the stage 12. The stage 12 is moved in a Y-axis direction with respect to the stand 11 by a Y-axis drive mechanism, which is not shown in the drawings.

The X-axis guide 13 is provided along an X-axis direction. The X-axis guide 13 is supported by support parts 11a and 11b that extend in an upward direction from the side surfaces of the stand 11.

The moving part 14 is attached to the X-axis guide 13. The moving unit 14 is moved along the X-axis guide 13 by an X-axis drive mechanism, which is not shown in figures. Further, the moving unit 14 is moved: in a Z-axis direction by a Z-axis drive mechanism, which is not shown in the drawings.

The first measurement part 15 and the second measurement part 16 are provided to face the workpiece W in a lower part of the moving unit 14. The first measurement part 15 and the second measurement part 16 radiate the visible light or the special light onto the workpiece W to acquire an image of the workpiece W. The details will be described later, but filter modules including optical filters for the special light are detachably mounted on the first measurement part 15 and the second measurement part 16.

The control unit 20 controls an operation of the vision measuring machine 10. For example, the control unit 20 controls the first measurement part 15 and the second measurement part 16. Further, the details will be described later, but the control unit 20 automatically switches one or more set values for adjustment (specifically, the set value of offset calibration and the like) used in a measurement in accordance with the type of the optical filters of the filter modules that are mounted on the first measurement part 15 and the second measurement part 16. In this manner, an operator does not have to adjust the set value in accordance with the optical filter when the operator replaces the filter module.

<Internal Configurations of the First Measurement Part 15 and the Second Measurement Part 16>

Hereinafter, the internal configuration of the first measurement part 15 is described with reference to FIGS. 2 to 6, and then the internal configuration of the second measurement part 16 is described with reference to FIG. 7.

[Internal Configuration of the First Measurement Part 15]

Figure 2:
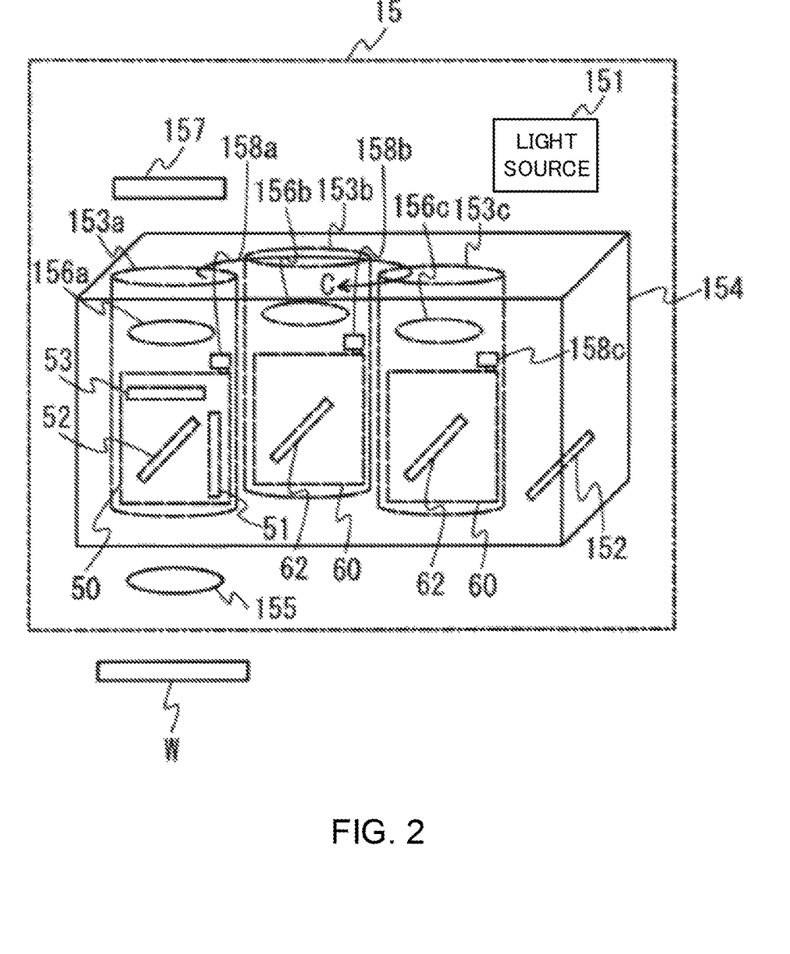
FIG. 2 is a schematic diagram for describing an example of an internal configuration of a first measurement part 15.

FIG. 2 is a schematic diagram for describing an example of the internal configuration of the first measurement part 15. As shown in FIG. 2, the first measurement part 15 includes a light source 151, a mirror 152, detachable parts 153*a* to 153*c*, a power turret 154, an objective lens 155, tube lenses 156*a* to 156*c*, an imaging part 157, and detection parts 158*a* to 158*c*.

The light source 151 includes, for example, a halogen lamp, a discharge lamp, a light emitting diode, or the like. The light source 151 emits the visible light or the special light to irradiate the mirror 152 (see FIG. 5). The light source 151 emits, for example, fluorescent excitation light or infrared light as the special light. The light source 151 emits the infrared light when, for example, the workpiece W is a circuit board made of silicon or the like. Further, the light source 151 emits the fluorescent excitation light when, for example, the workpiece W is an IC wafer. It should be noted that fluorescent excitation light has a characteristic that, after the excitation light is absorbed by dye molecules of a fluorescent substance formed on a surface of the workpiece W, the fluorescent substance emits fluorescence in accordance with its thickness.

The mirror 152 reflects the visible light or the special light (the fluorescent excitation light or the infrared light) radiated from the light source 151 toward a beam splitter in a detachable part located at a measurement position among the three detachable parts 153*a* to 153*c*.

The detachable parts 153*a* to 153*c* are arranged at predetermined intervals in the power turret 154 along the circumferential direction. The detachable parts 153*a* to 153*c* are rotatable in a predetermined direction (a direction of an arrow C shown in FIG. 2) along the circumferential direction. Optical modules (specifically, the filter module 50 or a visible light module 60) are respectively mounted on the detachable parts 153*a* to 153*c*. Here, the filter module 50 is mounted on the detachable part 153*a*, and the visible light modules 60 are mounted on the detachable part 153*b* and the detachable part 153*c*. It should be noted that the filter module 50 herein is a module including an optical filter for infrared light. The visible light module 60 is a module without an optical filter.

Figure 3:
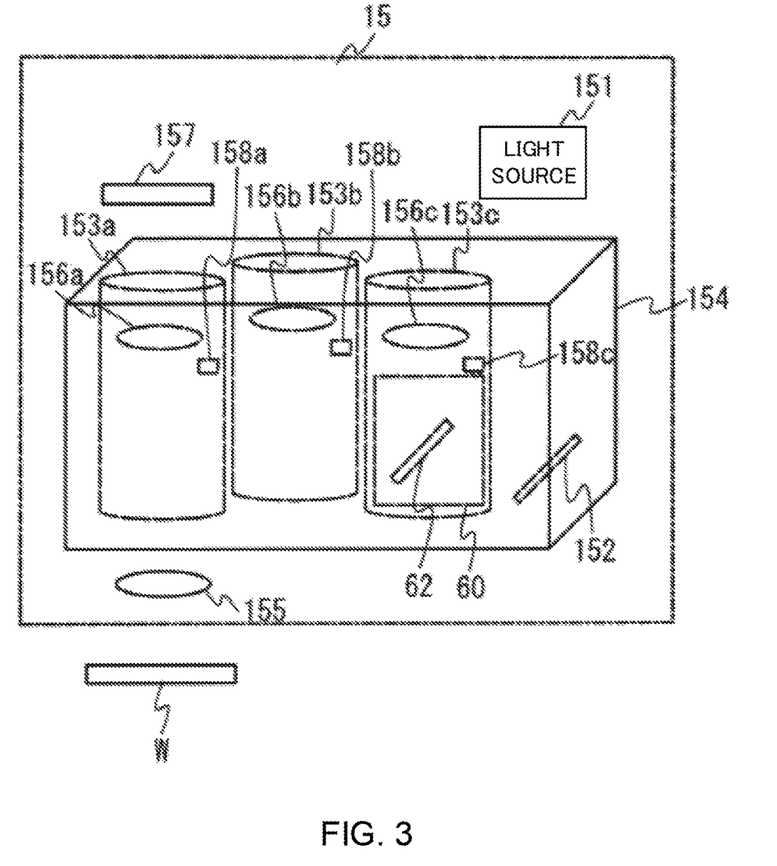
FIG. 3 is a schematic diagram showing a state where a filter module 50 and a visible light module 60 are detached from detachable parts 153a and 153b.

FIG. 3 is a schematic diagram showing a state where the filter module 50 and the visible light module 60 are detached from the detachable parts 153*a* and 153*b*. The filter module 50 and the visible light module 60 mounted on the detachable parts 153*a* to 153*c* can be detached. For example, after the operator detaches the filter module 50 for infrared light from the detachable part 153*a* the operator can mount another filter module (for example, a filter module 70 for fluorescent excitation light shown in FIG. 7) on the detachable part 153*a*.

Figure 4A:
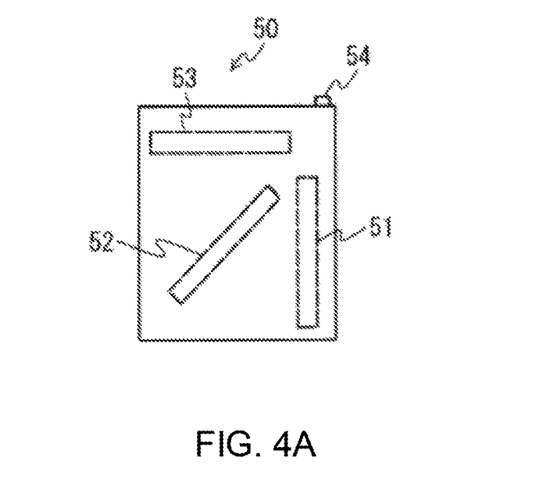
FIG. 4A is a schematic diagram for describing configurations of the filter module 50.
Figure 4B:
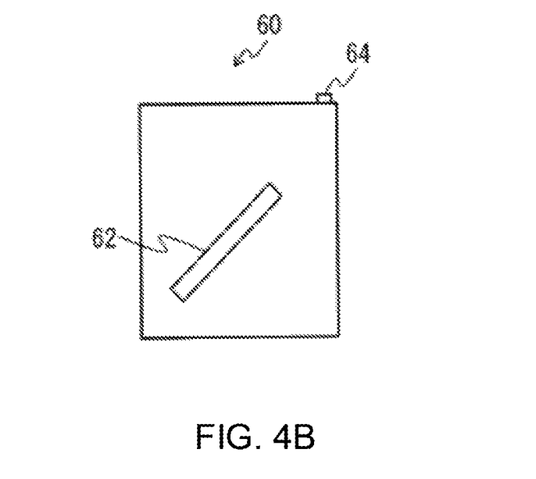
FIG. 4B is a schematic diagram for describing configurations of the visible light module 60.
Figure 5:
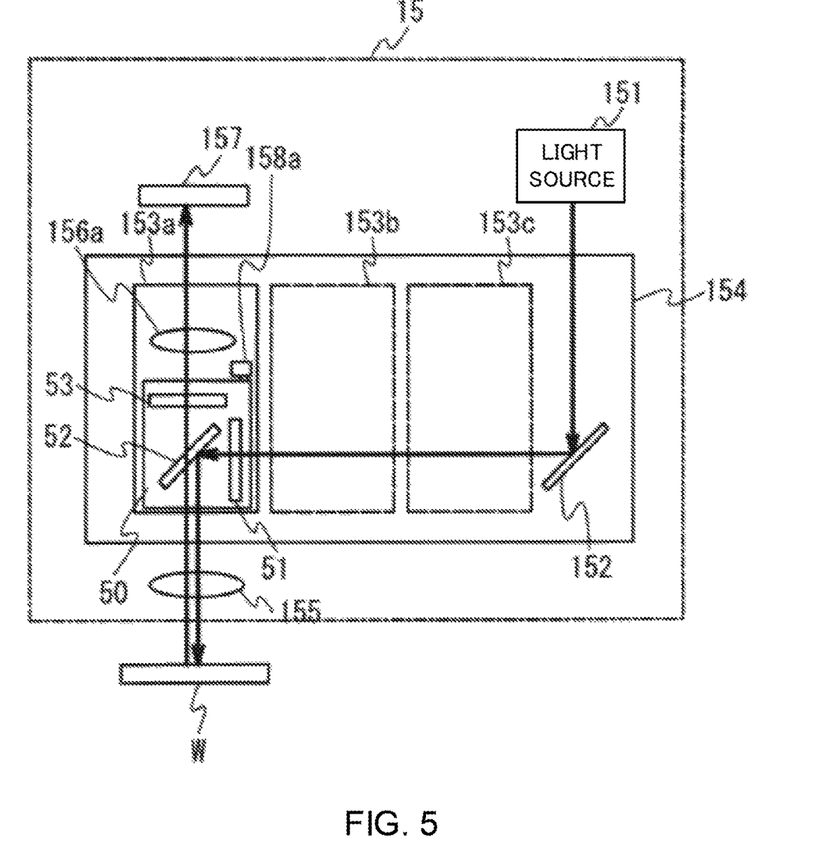
FIG. 5 is a schematic diagram for describing an optical path of infrared light.
Figure 6:
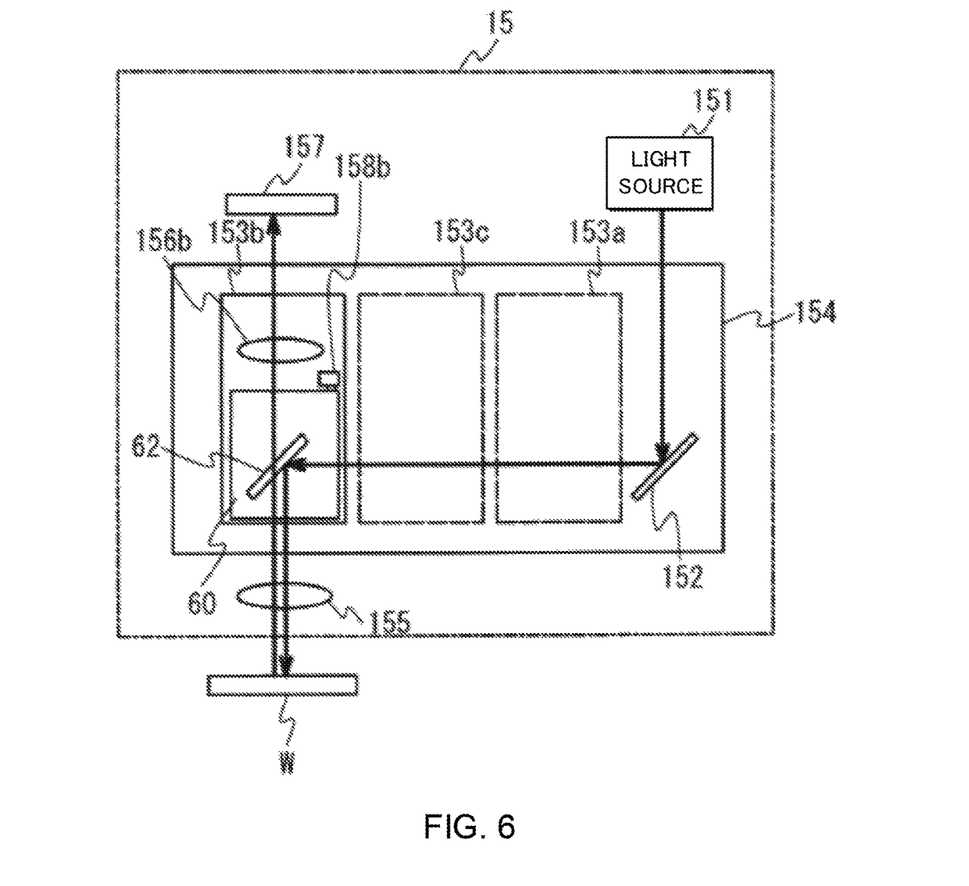
FIG. 6 is a schematic diagram for describing an optical path of visible light.

FIGS. 4A and 4B are schematic diagrams for describing configurations of the filter module 50 and the visible light module 60. FIG. 5 is a schematic diagram for describing an optical path of infrared light FIG. 6 is a schematic diagram for describing an optical path of visible light. It should be noted that FIG. 4A shows the filter module 50 for infrared light and FIG. 4B shows the visible light module 60 for visible light.

As shown in FIG. 4A, the filter module 50 has an infrared transmission filter 51, a beam splitter 52, a high-pass filter 53, and a connection part 54. It should be note that the infrared transmission filter 51 corresponds to a first optical filter and the high-pass filter 53 corresponds to a second optical filter.

As shown in FIG. 5, the infrared transmission filter 51 is an optical filter that transmits only the infrared light out of the light emitted from the light source 151. The beam splitter 52 reflects the infrared light transmitted through the infrared transmission filter 51 to the objective lens 155. In addition, the beam splitter 52 transmits return light from the workpiece W.

The high-pass filter 53 is an optical filter that transmits only the infrared light out of the return light from the workpiece W, the return light having passed through the beam splitter 52. The connection part 54 is a portion exposed to the outside from the filter module 50. The connection part 54 includes a resistance having a predetermined resistance value. The connection part 54 is connected to the detection part 158*a* when the filter module 50 is mounted on the detachable part 153*a*. Then, the filter module 50 can be specified by detecting the resistance value by the detection part 158*a*.

As shown in FIG. 4B, the visible light module 60 includes the beam splitter 67 and the connection part 64, but the visible light module 60 includes no optical filter, unlike the filter module 50.

As shown in FIG. 6, the beam splitter 62 reflects the visible light reflected by the mirror 152 to the objective lens 155. Further, the beam splitter 62 transmits the return light from the workpiece W. The connection part 64 is a portion exposed to the outside from the visible light module 60. The connection part 64 includes a resistance having a predetermined resistance value. The resistance value of the resistance of the connection part 64 is different from the resistance value of the resistance of the connection part 54 of the filter module 50. The connection part 64 is connected to the detection part 158*b* when the visible light module 60 is mounted on the detachable part 153*b*.

Returning to FIG. 2, the power turret 154 functions as a rotation part that rotates the three detachable parts 153*a* to 153*c*. The power turret 154 positions one detachable part out of the three detachable parts 153*a* to 153*c* at the measurement position located on the optical axis of the return light traveling from the workpiece W to the imaging part 157. In addition, the power turret 154 switches the tube lenses 156*a* to 156*c* provided in the detachable parts 153*a* to 153*c* by rotating the three detachable parts 153*a* to 153*c*.

For example, when the light source 151 emits the infrared light, the power turret 154 positions the detachable part 153*a*, on which the filter module 50 is mounted, at the measurement position, as shown in FIG. 5. Further, when the light source 151 emits the visible light, the power turret 154 positions the detachable part 153b, on which the visible light module 60 is mounted, at the measurement position, as shown in FIG. 6. It should be noted that, for the sake of convenience of explanation, the visible light modules 60 mounted on the detachable parts 153b and 153c are omitted in FIG. 5, and the filter module 50 and the visible light module 60 mounted on the detachable parts 153a and 153c are omitted in FIG. 6.

The objective lens 155 is configured to face the workpiece W. The objective lens 155 transmits the visible light or the special light. In addition, the objective lens 155 transmits the return light from the workpiece The tube lenses 156a to 156c are respectively provided in the detachable parts 153a to 153c. Specifically, the tube lenses 156a to 156c are provided above the filter module 50 and the visible light module 60. The tube lenses 156a to 156c are three optical lenses, each having different magnification. The tube lenses 156a to 156c transmit the return light front the workpiece W after varying the return light with a predetermined magnification. The return light having passed through the tube lenses 156a to 156c enters the imaging part 157.

The imaging part 157 captures an image of the workpiece W on the basis of the return light from the workpiece W. The imaging part 157 includes, for example, an image sensor such as a CCD sensor and a CMOS sensor. The imaging part 157 outputs the captured image of the workpiece W to the control unit 20. The control unit 20, for example, displays the image of the workpiece W on the display device.

The detection parts 158a to 158c detect the filter module 50 or the visible light module 60 mounted on the detachable parts 153a to 153c. For example, when the filter module 50 is mounted on the detachable part 153a, the detection part 158a detects the resistance value of the resistance of the connection part 54 of the filter module 50.

[Internal Configuration of the Second Measurement Part 16]

Figure 7:
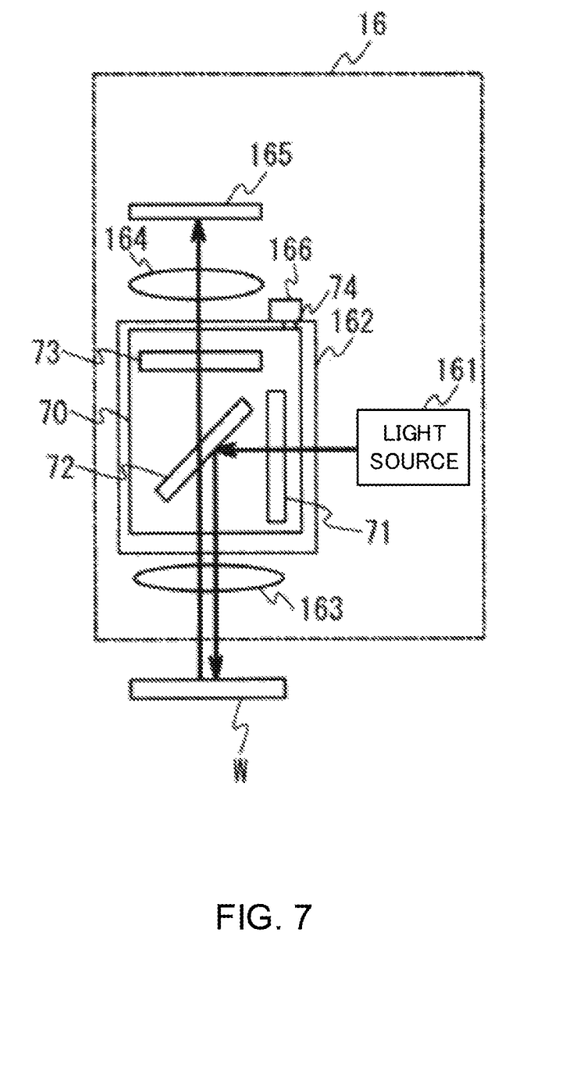
FIG. 7 is a schematic diagram for describing an example of an internal configuration of a second measurement part 16.

FIG. 7 is a schematic diagram for describing an example of the internal configuration of the second measurement part 16. As shown in FIG. 7, the second measurement part 16 includes a light source 161, a detachable part 162, an objective lens 163, a tube lens 164, an imaging part 165 and a detection part 166.

The light source 161 includes, for example, a halogen lamp, a discharge lamp, a light emitting diode, and the like. The light source 161 emits the visible light or the special light. The light source 161 emits, for example, fluorescent excitation light or infrared light as the special light.

An optical module (specifically, a filter module or a risible light module) is mounted on the detachable part 162. Here, the filter module 70 is mounted on the detachable part 162. The filter module 70 herein is a module including an optical filter for fluorescent excitation light. The filter module 70 includes an excitation filter 71, a beam splitter 72, a fluorescence filter 73, and a connection part 74.

The excitation filter 71 is an optical filter that transmits only the fluorescent excitation light having a wavelength that causes the workpiece W to emit fluorescence out of the light emitted from the light source 161. The beam splitter 72 reflects the fluorescent excitation light transmitted through the excitation filter 71 to the objective lens 163. In addition, the beam splitter 72 transmits the return light from the workpiece W.

The fluorescence filter 73 is an optical filter that transmits only the fluorescence out of the return light from the workpiece W, the return light having passed through the beam splitter 72. The connection part 74 is a portion exposed to the outside from the filter module 70. The connection part 74 includes a resistance having a predetermined resistance value. The connection part 74 is connected to the detecting part 166 when the filter module 70 is mounted on the detachable part 162.

The objective lens 163 is configured to face the workpiece W. The objective lens 163 transmits the visible light or the special light. In addition, the objective lens 163 transmits the return light from the workpiece W.

The tube lens 164 transmits the return light (here, the fluorescence), that has passed through the beam splitter 72 after varying the return light with the predetermined magnification. The return light having passed through the tube lens 164 enter the imaging part 165.

The imaging part 165 captures an image of the workpiece W on the basis of the return light from the workpiece W. The imaging part 165 includes, for example, an imaging sensor such as a CCD sensor or a CMOS sensor. The imaging part 165 outputs the captured image of the workpiece W to the control unit 20.

The detection part 166 detects the optical module detachably mounted on the detachable part 162. For example, when the filter module 70 is mounted on the detachable part 162, the detection part 166 detects the filter module 70 by measuring the resistance value of the resistance of the connection part 74.

It should be noted that, in the above description, the filter module 50 for an infrared light is mounted on the first measurement part 15, but it is not so limited. For example, the filter module 70 for fluorescent excitation light may be mounted on the first measurement part 15 in addition to the filter module 50. In such a case, by rotating the three detachable parts 153a to 153c, i) image acquisition of the workpiece W by the visible light and ii) image acquisition of the workpiece W by each of the two types of special light become possible without moving the moving part 14 and the workpiece W.

Further, in the above description, infrared light and fluorescent excitation light are described as examples of the special light, but it is not so limited. For example, polarized light may be used as the special light.

<Switching the Set Value for an Adjustment>

As described above, the filter modules 50 and 70 for various types of special light are detachably mounted on the detachable parts 153a to 153c of the first measurement part 15 and the detachable part 162 of the second measurement part 16. The appropriate set value (a set value for adjustment) of offset calibration and the like, while the vision measuring machine 10 is acquiring an image of the workpiece W, are different for each of the optical filters in the filter modules. Therefore, in the present exemplary embodiment, when the filter module is mounted, the set value for adjustment used in a measurement is automatically switched to the set value corresponding to the filter module. Such switching of the set value for adjustment is executed by the control unit 20.

Figure 8:
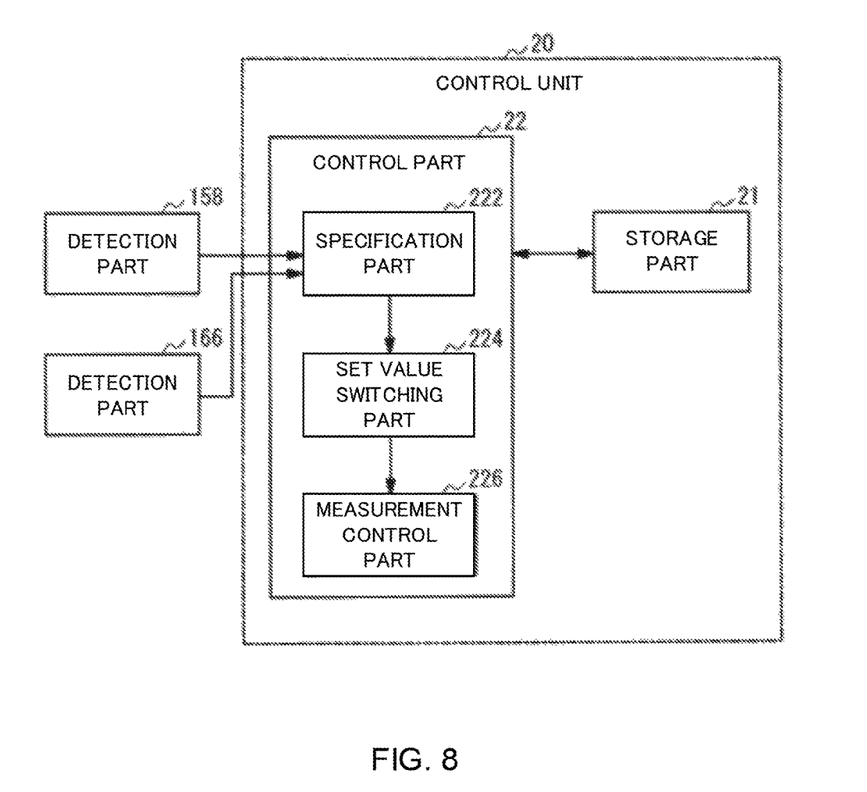
FIG. 8 is a block diagram showing an example of a configuration of a control unit 20.

FIG. 8 is a block diagram showing an example of a configuration of the control unit 20. The control unit 20 includes a storage part 21 and a control part 22.

The storage part 21 includes a Read Only Memory (ROM) and a Random Access Memory (RAM). The storage part 21 stores a program to be executed by the control part 22 and various pieces of data. For example, the storage part 21 stores the resistance value of the connection part of each filter module. In addition, the storage part 21 stores set information associating the optical filter of each filter module with the set value for adjustment.

The control part 22 is, for example, a Central Processing Unit (CPU). The control part 22 controls the operation of the vision measuring machine 10 by executing the program stored in the storage part 21. In the present exemplary embodiment, the control part 22 functions as a specification part 222, a set value switching part 224, and a measurement control part 226.

The specification part 222 specifies the optical filters of the filter modules mounted on the detachable parts 153a to 153c of the first measurement part 15 or the optical filter of the filter module mounted on the detachable part 162 of the second measurement part 16. For example, when the filter module 50 is mounted on the detachable part 153a, the specification part 222 specifies two optical filters (specifically, the infrared transmission filter 51 and the high-pass filter 53) of the filter module 50.

As described above, i) the resistances, each having a different resistance value, are provided in the filter modules 50 and 70, ii) the detection parts 158a to 158c (here, collectively referred to as a detection part 158 as shown in FIG. 8) specify the resistance values of the filter modules mounted on the detachable parts 153a to 153c, and iii) the detecting part 166 detects the resistance value of the filter module mounted on the detachable part 162. Then, the specification part 222 specifies the optical filter of the filter module on the basis of the resistance values detected by the detection parts 158 and 166.

The specification part 222 can specify the filter modules 50 and 70, and can also specify the visible light module 60. That is, the specification part 222 can distinguish the filter modules 50 and 70 from the visible light module 60 mounted on the detachable parts 153a to 153c.

The set value switching part 224 switches the set value for adjustment used in a measurement by using the specific optical filter in accordance with the specific optical filter specified by the specification part 222. For example, the set value switching part 224 switches a set value for adjustment to the set value for adjustment corresponding to the specific optical filter on the basis of the specific optical filter specified by the specification part 222 and the set information (information associating the optical filter and the set values for adjustment with each other) stored in the storage part 21. The set value for adjustment is, for example, a set value for an offset calibration, for a lens calibration, or for an illumination calibration. The set value switching part 224 switches each of the set values of the offset calibration, the lens calibration, and the illumination calibration in accordance with the optical filter specified by the specification part 222.

Here, the offset calibration means adjustment of the amount of deviation in the X, Y, and Z-axis directions of the first measurement part 15 and the second measurement part 16. The lens calibration means adjustment of the size of the image of the workpiece W within the display screen. The illumination calibration means adjustment of an intensity of the light of the light sources 151 and 161.

The set value switching part 224 switches the set values for adjustment for each of the filter modules mounted on each of the plurality of detachable parts 153a to 153c. In such a manner, a single device can acquire an image of the workpiece W with a plurality of types of the special light.

The measurement control part 226 controls the measurement by the first measurement part 15 and the second measurement part 16. The measurement control part 226 performs the measurement on the basis of the set value for adjustment that is switched by the set value switching part 224. Specifically, the measurement control part 226 performs the measurement by using the set value for adjustment corresponding to the filter modules mounted on the detachable part located at the measurement position out of the three detachable parts 153a to 153c. As a result, the measurement can be performed with high accuracy.

<Operation Example of the Measurement System 1>

An operation example of the measurement system 1 when the set values for adjustment are switched will be described with reference to FIG. 9.

Figure 9:
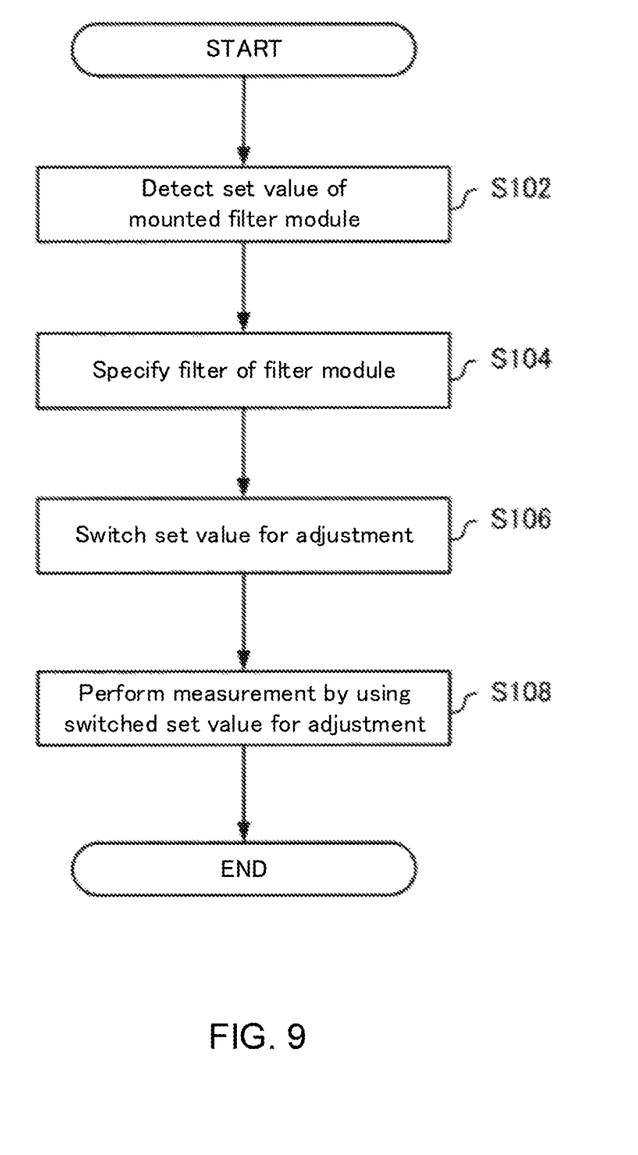
FIG. 9 is a flowchart for describing an operation example of the measurement system 1 when set values for adjustment are switched.

FIG. 9 is a flowchart for describing the operation example of the measurement system 1 when the set values for adjustment are switched. This operation is realized by the control part 22 of the control unit 20 executing the program stored in the storage part 21.

The flow chart in FIG. 9 starts from the time when the filter module 50 is mounted on the detachable part 153a of the first measurement part 15. The detection part 158a detects the resistance value of the filter module 50 mounted on the detachable part 153a (step S102). For example, the detection part 158a detects the resistance value of the resistance of the connection part 54 of the filter module 50.

Next, the specification part 222 specifies the filter module 50 mounted on the detachable part 153a on the basis of i) the magnitude of the resistance value detected by the detection part 158a and ii) the corresponding relation between the resistance value and the filter module (including information about the optical filter in the filter module) stored in the storage part 21 (step S104). Here, the specification part 222 specifies the optical filter of the filter module 50 mounted on the detachable part 153a on the basis of the magnitude of the resistance value detected by the detection part 158a.

Next, in accordance with the specific optical filter specified by the specification part 222, the set value switching part 224 switches the set values for adjustment used in a measurement using the specific optical filter (step S106). For example, the set value switching part 224 switches to the set values for adjustment corresponding to the specific optical filter with reference to the corresponding relation between the optical filter and the set values for adjustment stored in the storage part 21.

Then, the measurement control part 226 performs a measurement by using the set values for adjustment that were switched by the set value switching part 224 when the measurement is performed in a state where the detachable part 153a, on which the filter module 50 is mounted, is positioned at the measurement position (step S108). As a result, the measurement is performed with the set values for adjustment optimal for the optical filter of the filter module 50.

<Effect of the Present Exemplary Embodiment>

The above-described measurement system 1 specifies the optical filter of the filter module mounted on the detachable part (the detachable parts 153a to 153c and the detachable part 162). In such a manner, the filter module mounted on each of the detachable parts can be specified even when various filter modules for special light are mounted on the detachable parts 153a to 153c and the detachable part 162. Further, the measurement system 1 switches, in accordance with the specified optical filter, the set values for adjustment used in a measurement using the optical filter. In this manner, when the measurement by the special light is performed by using the filter module mounted on any of the detachable parts 153a to 153c and the detachable part 162, the measurement can be performed with the set values for adjustment that are appropriate for the optical filter of the filter module. As a result, an optimum measurement can be performed.

According to the measurement system 1, even when a plurality of vision measuring machines are not used, it is possible to acquire images of the workpiece W with a plurality of types of special light using one vision measuring machine 10. Furthermore, the number of the types of workpiece W that can be measured is increased by replacing the filter module. Moreover, since it is possible for the one vision measuring machine 10 to acquire the images of the workpiece W using a plurality of types of special light, it is possible to realize high speed measurement and a reduction of the cost required for measurement.

The present invention is explained with the exemplary embodiments of the present invention but the technical scope of the present invention is not limited to the scope described in the above embodiment. It is apparent for those skilled in the art that it is possible to make various changes and modifications to the embodiment. It is apparent from the description of the scope of the claims that the forms added with such changes and modifications are included in the technical scope of the present invention.

What is claimed is:

1. A measurement system comprising:
   detachable parts, on which one filter module out of a plurality of filter modules including optical filters that each transmit different types of special light is detachably mounted;
   a specification part that specifies the optical filter of the one filter module by distinguishing the one filter module when the one filter module is mounted on the detachable parts; and
   a set value switching part that switches, as a set value of an offset calibration of a measuring machine, a set value of the offset calibration corresponding to the optical filter specified by the specification part.

2. The measurement system according to claim 1, wherein
   the plurality of the detachable parts are provided,
   the filter modules that are different from each other are mounted on the plurality of detachable parts, and
   the set value switching part switches the set values for adjustment for each of the filter modules mounted on each of the detachable parts.

3. The measurement system according to claim 2, further comprising:
   a rotation part that rotates the plurality of detachable parts; and
   a light source that emits the special light, wherein
   the rotation part positions the filter module mounted on the one detachable part out of the plurality of detachable parts at a transmission position where the special light from the light source passes through the optical filter of the filter module.

4. The measurement system according to claim 2, wherein
   visible light modules including optical members through which visible light passes are detachably mounted on the plurality of detachable parts, and
   the specification part distinguishes the filter module mounted on the detachable part from the visible light module.

5. The measurement system according to claim 1, wherein
   the set value switching part switches a plurality of set values for adjustment in accordance with the optical filter specified by the specification part.

6. The measurement system according to claim 1, wherein
   the filter module includes, as the optical filter, a first optical filter that transmits the special light directed to the object to be measured and a second optical filter that transmits return lights from the object to be measured, and
   the specification part specifies the first optical filter and the second optical filter.

7. The measurement system according to claim 1, wherein
   the specification part specifies the optical filter on the basis of a resistance having a predetermined resistance value provided in a connection part of the filter module.

8. The measurement system according to claim 7, further comprising:
   a specification part that specifies the resistance value of the resistance of the connection part when the filter module is attached to the detachable parts, wherein
   the specification part specifies the optical filter of the filter module on the basis of the resistance value specified by the specification part.

9. The measurement system according to claim 1, further comprising:
   a storage part that stores set information associating the optical filter of the filter module with the set values for adjustment, wherein
   the set value switching part switches the set values for adjustment on the basis of the optical filter specified by the specification part and the set information stored in the storage part.

10. The measurement system according to claim 1, wherein
    the special light includes infrared light and fluorescent excitation light.

11. A method for switching set values for adjustment of a measurement system including detachable parts, on which one filter module out of a plurality of filter modules having optical filters that each transmit a different type of special light is detachably mounted, the method comprising the steps of:
    specifying the optical filter of the one filter module by distinguishing the one filter module when the one filter module is mounted on the detachable parts; and
    switching, as a set value of an offset calibration of a measuring machine, a set value of the offset calibration corresponding to the specified optical filter.

12. The method for switching set values for adjustment according to claim 11, wherein
    the plurality of the detachable parts are provided,
    the filter modules that are different from each other are mounted on the plurality of detachable parts, and
    the specification step switches the set values for adjustment for each of the filter modules mounted on each of the detachable parts.

13. The method for switching set values for adjustment according to claim 11, wherein
    visible light modules including optical members through which visible light passes are detachably mounted on the plurality of detachable parts, and
    the specification step distinguishes the filter module mounted on the detachable part from the visible light module.

14. The method for switching set values for adjustment according to claim 11, wherein
    the specification step specifies the optical filter on the basis of a resistance having a predetermined resistance value provided in a connection part of the filter module.

15. The method for switching set values for adjustment according to claim 11, wherein
    the switching step switches the set values for adjustment on the basis of the optical filter specified by the specification step and the set information, associating the optical filter of the filter module with the set values for adjustment, stored in the storage part.

* * * * *